United States Patent [19]

Karrer et al.

[11] Patent Number: 5,747,411
[45] Date of Patent: May 5, 1998

[54] SUPPORTED CATALYSTS WHICH ARE SUITABLE FOR AMMONOXIDATION

[75] Inventors: Lothar Karrer, Pfungstadt; Frank-Friedrich Pape, Kleinniedesheim; Ulrich Köhler, Mannheim; Rainer Becker, Bad Dürkheim; Peter Weidlich, Mannheim; Michael Hüllmann, Bensheim; Heinz-Josef Kneuper, Mannheim, all of Germany

[73] Assignee: BASF Aktiengesellschaft, Ludwigshafen, Germany

[21] Appl. No.: 513,740

[22] Filed: Aug. 10, 1995

[30] Foreign Application Priority Data

Aug. 12, 1994 [DE] Germany ............... 44 28 595.7

[51] Int. Cl.⁶ ............... B01J 23/18; B01J 23/22; C07C 253/24
[52] U.S. Cl. ............... 502/353; 502/354; 558/325; 558/328
[58] Field of Search ............... 502/354, 353; 558/325, 328

[56] References Cited

U.S. PATENT DOCUMENTS

| | | | |
|---|---|---|---|
| 3,637,797 | 1/1972 | Decker et al. | 260/465 C |
| 4,044,042 | 8/1977 | Angstadt | 260/465 C |
| 4,178,304 | 12/1979 | Litvishkov et al. | 260/465 E |
| 4,271,091 | 6/1981 | Grasselli et al. | 564/305 |
| 4,336,205 | 6/1982 | Onishi et al. | 260/465 C |
| 4,582,911 | 4/1986 | Wachs et al. | 549/239 |
| 4,814,479 | 3/1989 | Engelbach et al. | 558/328 |
| 4,877,764 | 10/1989 | Glaeser et al. | 502/209 |
| 4,952,389 | 8/1990 | Szymanske et al. | 423/625 |
| 5,332,855 | 7/1994 | Blanchard et al. | 558/319 |

FOREIGN PATENT DOCUMENTS

| | | |
|---|---|---|
| 222 249 | 5/1987 | European Pat. Off. . |
| 352 023 | 1/1990 | European Pat. Off. . |
| 389 701 | 10/1990 | European Pat. Off. . |
| 668 424 | 9/1992 | European Pat. Off. . |
| 28 10 856 | 10/1979 | Germany . |

*Primary Examiner*—Glenn Caldarola
*Assistant Examiner*—Alexander G. Ghyka
*Attorney, Agent, or Firm*—Keil & Weinkauf

[57] ABSTRACT

Supported catalysts which are suitable for ammonoxidation, comprising a) a spherical or approximately spherical support material which essentially comprises aluminum oxide, silicon dioxide, titanium dioxide and/or zirconium dioxide and whose bulk density is from 0.6 to 1.2 kg/l, and b) an active material which comprises, as essential components, vanadium and antimony in oxidic form.

17 Claims, No Drawings

SUPPORTED CATALYSTS WHICH ARE SUITABLE FOR AMMONOXIDATION

The present invention relates to supported catalysts which are suitable for ammonoxidation, comprising
a) a spherical or approximately spherical support material which essentially comprises aluminum oxide, silicon dioxide, titanium dioxide and/or zirconium dioxide and whose bulk density is from 0.6 to 1.2 kg/l, and
b) an active material which comprises, as essential components, vanadium and antimony in oxidic form.

The present invention furthermore relates to a process for the preparation of these supported catalysts and to their use for the ammonoxidation of isoaromatic and heteroaromatic alkyl compounds to the corresponding nitriles.

The ammonoxidation of $C_1$–$C_4$-alkyl-isoaromatic and -heteroaromatic compounds, such as toluene, xylenes or picolines, is a conventional industrial process for the synthesis of the corresponding aromatic nitriles. The reaction is usually carried out in the gas phase in the presence of supported catalysts comprising, in addition to vanadium, other elements such as antimony, chromium, molybdenum or phosphorus in oxidic form. The supports are principally inert metal oxides, such as aluminum oxide, silicon dioxide, titanium oxide or zirconium dioxide, or mixtures thereof.

Since ammonoxidation, which is a highly exothermic process, is usually carried out in industry in fluidized-bed reactors, high demands are made of the catalysts with respect to the fluidizability, the abrasion resistance and the heat-transfer ability which have hitherto not been satisfactorily achieved. In particular, the abrasion resistance of these catalysts is unsatisfactory. Abrasion produces fine catalyst dust, which is removed from the fluidizing zone and can cause undesired secondary reactions outside it.

Good heat transfer can be achieved if the bulk density of the catalyst is high; however, the requirement for fluidizability means that there is an upper limit to the bulk density.

The catalysts are currently prepared by a process which has been known for some time and has merely been slightly modified in the course of time. For example, DE-A 28 10 856 and EP-A 222 249 relate to processes in which aluminum oxide is ignited at 900° C., comminuted and screened. The desired fraction is impregnated with a solution of the active constituents of the catalyst, the mixture is then evaporated, and the material which remains is dried, calcined under oxidizing conditions and then comminuted. A similar process is described in DE-A 16 43 630 (U.S. Pat. No. 3,637,797). This gives needle-shaped particles with which the fluidized-bed process, due to their low bulk density of about 0.5 kg/l, can, in industry, only be controlled in a complex manner. In addition, the low bulk density of the particles means that they have unsatisfactory heat-transfer ability.

It is an object of the present invention to overcome said disadvantages.

We have found that this object is achieved by the supported catalysts defined at the outset and by a process for the preparation of these supported catalysts and by their use for ammonoxidation.

The spherical or approximately spherical support material is known per se and commercially available (for example various grades of Puralox® from Condea-Chemie, Moers, in the case of aluminum oxide). However, support materials of this type have hitherto not been employed for ammonoxidation.

Suitable spherical particles preferably have a mean shape factor F of >85%. The shape factor is defined as $$F=(U_2)^2/(U_1)^2$$

where $U_1$ is the circumference of a particle cross section Q, and $U_2$ is the circumference of a circle having the same cross-sectional area Q. The condition of a minimum shape factor is satisfied when no cross section of the particle corresponds to a smaller value, as can be determined statistically.

The support material can be prepared by spray-drying the solution or suspension of an aluminum, silicon, titanium and/or zirconium compound and converting the resultant particles into the oxides in an oxygen-containing gas stream at from 500° to 1200° C. During spray-drying, the desired particle size and bulk density can be established in a manner known per se. The bulk density of the support material is, in accordance with the invention, from 0.6 to 1.2 kg/l, preferably from 0.7 to 1.0 kg/l.

For the production of the spherical particles by spray-drying of solutions, suitable compounds are, for example, alkoxides, such as ethoxides and isopropoxides, carboxylates, such as acetates, sulfates and nitrates, and, as suspended compounds, hydroxides and oxide hydrates.

The calcined support material is then impregnated with a solution or suspension of compounds of the active material, and the resultant material is then dried in a manner known per se and calcined in a stream of air. The drying is preferably carried out at from 100° to 200° C. and the calcination at from 400° to 750° C.

The impregnation is preferably carried out using aqueous solutions or suspensions of the compounds of the active catalyst constituents, but in principle any liquids are suitable. The impregnation solution or suspension is preferably not employed in a larger amount than can be absorbed by the support material, since otherwise drying gives agglomerates, which must first be recomminuted, forming particles which do not have the desired spherical shape. The impregnation can also be carried out in a plurality of steps with interim drying after each one.

The amount of vanadium, calculated as metal, in the active catalyst is generally from 0.5 to 10% by weight, preferably from 1.0 to 6% by weight, in particular from 1.5 to 5% by weight, and the amount of antimony, likewise calculated as metal, is from 0.5 to 10% by weight, preferably from 0.5 to 8% by weight, in particular from 0.5 to 6% by weight.

Particularly effective catalysts for ammonoxidation additionally contain from 0.01 to 2.0% by weight of cesium and/or rubidium, calculated as metal. A content of from 0.05 to 1.5% by weight of tungsten, calculated as the metal, has also proven favorable. The amount data are in each case based on the total weight of the catalyst.

In addition, the active catalyst material can contain further components, for example titanium, iron, cobalt, nickel, manganese or copper, as proposed in the ammonoxidation references.

For the impregnation of the support material, the active components are preferably employed in the form of aqueous solutions of their salts, in particular of salts of organic acids which decompose on oxidative calcination without leaving a residue. Preference is given here to the oxalates, particularly in the case of vanadium, and the tartrates, particularly in the case of antimony; the tartrates can also be in the form of mixed salts, for example with ammonium ions. In order to prepare such solutions, the metal oxides can be dissolved in the acids. Tungsten is preferably employed in the form of complex compounds with tartaric acid, oxalic acid or citric acid.

The novel catalysts are particularly suitable for ammonoxidation in a fluidized bed. This technique is known per se, making further details superfluous.

In particular, the catalysts are used for the preparation of isoaromatic and heteroaromatic mono- and polynitriles from the corresponding alkyl compounds, in particular the methyl compounds.

Ammonoxidation is particularly important for the preparation of o-phthalonitrile from o-xylene, of isophthalonitrile from m-xylene, of terephthalonitrile from p-xylene, of benzonitrile from toluene and of nicotinonitrile from β-picoline.

In the case of xylenes, the ammonoxidation of the first methyl group proceeds more quickly than that of the second, which means that partial ammonoxidation products, for example p-methylbenzonitrile from p-xylene, can also easily be obtained.

The aromatic parent compounds can carry substituents which are inert under the ammonoxidation conditions, for example halogen, trifluoromethyl, nitro, amino or cyano. Non-inert substituents are also possible if they are converted into desired substituents under the ammonoxidation conditions, for example aminomethyl or hydroxymethyl.

In a preferred procedure, the starting compounds are taken up in a gas stream comprising ammonia and an oxygen-containing gas, such as air, with their concentration expediently being set to from 0.1 to 25% by volume, preferably from 0.1 to 10% by volume.

The novel catalysts allow a space velocity over the catalyst of from 0.01 to 1 kg of starting compound per kg of catalyst and per hour. They have the great advantage that the fluidized bed remains constant over long operating times and therefore does not require complex regulation. The formation of undesired byproducts is suppressed, and the yields of the desired products is correspondingly significantly increased.

EXAMPLE 1

Preparation of a Supported Catalyst 1000 g of spherical aluminum oxide (Puralox® SCCa 150/120 from Condea-Chemie, Moers), which had a shape factor of 0.85 and a bulk density of 0.8 kg/l, was impregnated in a mixer with 931.9 g of an aqueous solution prepared from 351.4 g of distilled water, 150 g of 25% strength $NH_3$ solution, 65.5 g of antimony(III) oxide, 56.2 g of vanadic acid (90% of vanadium(V) oxide), 6.5 g of cesium nitrate, 150 g of tartaric acid and 152.3 g of oxalic acid dihydrate. The solution was fully adsorbed. The resultant material was dried at 120° C. and then calcined at 580° C. in a stream of air.

Ammonoxidation of o-xylene o-Xylene was reacted at 470° C. on this catalyst (0.75 l) in a gas stream comprising 3% by volume of o-xylene, 12% by volume of oxygen and 85% by volume of ammonia in a fluidized-bed trial reactor with a diameter of 6 cm and a height of 120 cm. An o-phthalonitrile yield of 64.6% (based on o-xylene) and an o-xylene conversion of 95.3% were achieved.

EXAMPLE 2

1000 g of spherical aluminum oxide (Puralox® SCC a 150/120 from Condea-Chemie, Moers), which had a bulk density of 0.8 kg/l, was impregnated in a mixer with 931.9 g of an aqueous solution prepared from 351.4 g of distilled water, 150 g of 25% strength $NH_3$ solution, 65.5 g of antimony(III) oxide, 56.2 g of vanadic acid (90% by weight of vanadium(V) oxide), 12.5 g of cesium nitrate, 150 g of tartaric acid and 152.3 g of oxalic acid dihydrate. In addition, 13.8 g of ammonium para-tungstate ($[NH_4]_{10}H_2W_{12}O_{42} \cdot 5H_2O$) which had previously been dissolved in 50 g of tartaric acid and 200 ml of water were added to the solution. The impregnated catalyst precursor was subsequently calcined in an oven at 580° C. for two hours. According to chemical analysis, the catalyst contained 1.0% by weight of tungsten.

Ammonoxidation of o-xylene o-Xylene was reacted at 470° C. on this catalyst (600 g) in a gas stream comprising 3.2% by volume of o-xylene (ie. 128 g/h), 12% by volume of oxygen and approximately 85% by volume of ammonia in a fluidized-bed trial reactor with a diameter of 6 cm and a height of 120 cm. The amount of o-xylene fed in was limited by coking of the catalyst, which resulted in a considerable drop in conversion at excessively high o-xylene metering rates. A yield of 65.0% of phthalonitrile (based on o-xylene) and an o-xylene conversion of 95.7% were achieved. Thus, 100.4 g of phthalonitrile were obtained per hour, based on 100 g of catalyst.

Comparative Example

Preparation of a supported catalyst

The catalyst was prepared by a similar method, but using a needle-shaped support material having a bulk density of 0.5 kg/l, as described in EP-A 222 249.

Ammonoxidation of o-xylene

A reaction carried out in a similar manner gave an o-xylene conversion of 95.8% and an o-phthalonitrile yield of 62.8% (based on o-xylene).

We claim:

1. A supported catalyst which is suitable for ammonoxidation, comprising
   a) a support material which essentially comprises aluminum oxide, silicon dioxide, titanium dioxide and/or zirconium dioxide, and
   b) an active material which comprises, as essential components, vanadium and antimony in oxidic form
   wherein the support material is spherical or approximately spherical and has a bulk density of from 0.6 to 1.2 kg/l.

2. A supported catalyst as claimed in claim 1, wherein the active material b) additionally comprises cesium and/or rubidium in oxidic form.

3. A supported catalyst as claimed in claim 1, additionally containing tungsten in oxidic form in the active material.

4. A supported catalyst as claimed in claim 1, comprising, based on the weight of the supported catalyst, from 0.5 to 10% by weight of vanadium and from 0.5 to 10% by weight of antimony, in each case calculated as metal.

5. A supported catalyst as claimed in claim 2, comprising, based on the weight of the supported catalyst, from 0.01 to 2% by weight of cesium and/or rubidium, calculated as metal.

6. A supported catalyst as claimed in claim 3, containing from 0.05 to 1.5% by weight of tungsten, calculated as metal, based on the weight of the supported catalyst.

7. A process for the preparation of a supported catalyst as claimed in claim 1, wherein a spherical or approximately spherical support material as defined is impregnated with a solution or suspension of a vanadium compound and of an antimony compound and, if desired, of a cesium and/or rubidium compound and of a tungsten compound, and the resultant mixture is separated from excess liquid, dried and calcined under oxidizing conditions.

8. A process for the preparation of a supported catalyst as claimed in claim 7, wherein the vanadium is employed in the form of a salt of oxalic acid.

9. A process for the preparation of a supported catalyst as claimed in claim 7, wherein the antimony is employed in the form of a salt of tartaric acid.

10. A process for the preparation of a supported catalyst as claimed in claim 7, wherein the tungsten is employed in the form of a complex compound with tartaric acid, oxalic acid or citric acid.

11. A process for the preparation of a supported catalyst as claimed in claim 7, wherein the calcination is carried out at from 400° to 750° C.

12. A process for the preparation of isoaromatic or heteroaromatic mono- or polynitriles by catalytic ammonoxidation of the corresponding isoaromatic or heteroaromatic alkyl compounds by means of an oxygen- and ammonia-containing gas, wherein a catalyst as claimed in claim 1 is used.

13. A process as claimed in claim 12, wherein the reaction is carried out at from 300° to 550° C.

14. A process as claimed in claim 12, wherein the oxygen content of the gas employed for the ammonoxidation is from 0.1 to 25% by volume.

15. A process as claimed in claim 12, wherein the reaction is carried out in a fluidized-bed reactor.

16. A process as claimed in claim 12, which is used for the ammonoxidation of xylenes to methylbenzonitriles or benzodinitriles.

17. A process as claimed in claim 12, which is used for the ammonoxidation of o-xylene to phthalonitrile.

* * * * *